United States Patent [19]

Sanderson

[11] Patent Number: 4,487,974

[45] Date of Patent: Dec. 11, 1984

[54] OXIDATION OF CYCLOHEXYLBENZENE TO 1-PHENYL CYCLOHEXYLHYDROPEROXIDE

[75] Inventor: John R. Sanderson, Austin, Tex.

[73] Assignee: Texaco Inc., White Plains, N.Y.

[21] Appl. No.: 469,183

[22] Filed: Feb. 24, 1983

[51] Int. Cl.³ .............................................. C07C 179/02
[52] U.S. Cl. ...................................... 568/570; 568/573
[58] Field of Search ......................... 568/570, 571, 573

[56] References Cited

U.S. PATENT DOCUMENTS

| 2,796,439 | 6/1957 | Bernis | 568/570 |
| 3,308,164 | 3/1967 | Shepard | 568/570 |
| 3,846,499 | 11/1974 | Reidl | 568/570 |
| 4,282,382 | 8/1981 | Wu | 568/570 |
| 4,282,383 | 8/1981 | Dai et al. | 568/573 |

FOREIGN PATENT DOCUMENTS

| 562743 | 9/1958 | Canada | 568/570 |
| 1059903 | 6/1959 | Fed. Rep. of Germany | 568/570 |

Primary Examiner—Werren B. Lone
Attorney, Agent, or Firm—Robert A. Kulason; Kenneth R. Priem; David L. Mossman

[57] ABSTRACT

A method of preparing 1-phenyl cyclohexylhydroperoxide by contacting a mixture of cyclohexylbenzene, an alkali or alkaline earth metal salt of cumene hydroperoxide, and an alkali or alkaline earth metal salt of phenol or a substituted phenol with an oxygen containing gas under effective reaction conditions of temperature and pressure.

9 Claims, No Drawings

OXIDATION OF CYCLOHEXYLBENZENE TO 1-PHENYL CYCLOHEXYLHYDROPEROXIDE

BACKGROUND OF THE INVENTION

This invention relates to a process for the air oxidation of cyclohexylbenzene and, more particularly, for an improved process using a sodium salt of phenol or a substituted phenol and a sodium salt of cumene hydroperoxide to increase the selectivity to the desired 1-phenyl cyclohexylhydroperoxide.

Co-assigned U.S. Pat. No. 3,959,381 sets forth a method of producing phenol and cyclohexanone by the air oxidation of cyclohexylbenzene, preferably in the presence of a material selected from the group consisting of cumene and cumene hydroperoxide.

U.S. Pat. No. 3,523,977 sets forth a method for the oxidation of cumene to cumene hydroperoxide in the presence of the sodium salt of cumene hydroperoxide and phenol. The quantity of phenol set forth in the patent is between about 0.001 and 0.1% by weight with respect to the amount of cumene charged to the reactor.

In U.S.S.R. Pat. No. 237,160, issued on Feb. 12, 1969, a method is set forth for the preparation of phenol and cyclohexanone which includes the oxidation of phenylcyclohexane at 115° to 120° C. in the presence of an initiator such as isopropylbenzene peroxide and an alkali additive such as soda, calcium oxide, calcium hydroxide, sodium hydroxide, sodium stearate or their combinations.

SUMMARY OF THE INVENTION

It now has been discovered that cyclohexylbenzene can be oxidized to 1-phenyl cyclohexylhydroperoxide in good yield and high selectivity by contacting a mixture of the cyclohexylbenzene, an alkali or alkaline earth metal salt of cumene hydroperoxide and an alkali or alkaline earth metal salt of phenol or a substituted phenol with an oxygen containing gas under effective reaction conditions of temperature and pressure. The 1-phenyl cyclohexylhydroperoxide can then be subjected to acid catalyzed cleavage to form phenol and cyclohexanone both of which are useful industrial chemicals.

PREFERRED EMBODIMENT OF THE INVENTION

In a preferred method of forming 1-phenyl cyclohexylhydroperoxide, a small quantity, between about 0.01 and about 1 percent by weight of an alkali or alkaline earth metal salt of cumene hydroperoxide and a small quantity, between about 0.005 and about 0.5 percent by weight of an alkali or alkaline earth metal salt of a phenol or a substituted phenol, are mixed with the cyclohexylbenzene. This mixture is then contacted with an oxygen containing gas, generally air, and the mixture is heated, preferably to a temperature of between about 80° and 140° C. The oxidation can be carried out at atmospheric pressure, under a vacuum of several atmospheres or at a super atmospheric pressure. The molar ratio of oxygen to cyclohexylbenzene used in the reaction is preferably from about 3 to 1 up to about 100 to 1 or more. The 1-phenyl cyclohexylhydroperoxide that is formed is then preferably separated from the reaction materials. The desired hydroperoxide is generally produced at relatively high conversion levels and at higher selectivities than without the use of the additives.

The alkali or alkaline earth metal salt of cumene hydroperoxide which is preferably added as a salt, as opposed to being formed in situ, has been found to improve the percentage of cyclohexylbenzene converted to the hydroperoxide under a given set of reaction conditions. The preferred alkali or alkaline earth metal salt comprises the sodium salt. However, other alkali or alkaline earth metal salts such as magnesium, aluminum, calcium, barium, lithium or potassium can also be used. The cumene hydroperoxide and its alkali or alkaline earth metal salt can be conventionally prepared, such as set forth in U.S. Pat. No. 3,523,977. The quantity of sodium cumene hydroperoxide added to the cyclohexylbenzene can be from about 0.01 percent by weight to about 1 percent by weight, and preferably from about 0.05 to about 0.5 percent by weight.

It has been unexpectedly found that the addition of an alkali or alkaline earth metal salt of phenol or a substituted phenol improves the selectivity to the 1-phenyl cyclohexylhydroperoxide without substantially inhibiting the production of the 1-phenyl cyclohexylhydroperoxide. The alkali or alkaline earth metal salt of the phenol or substituted phenol can be formed in-situ, or more preferably is added to the cyclohexylbenzene prior to oxidation. Phenol and substitute phenols are available commercially and can be manufactured by well-known processes. The substituted phenols can be mono, di- or tri-substituted. The substituents can be any one of the well known functional groups and can include among others, alkyl, cycloalkyl, alkenyl, cycloalkenyl, substituted cycloalkyl and cycloalkenyl, aryl, substituted aryl, halogen, sulfur containing groups, oxygen containing groups, nitrogen containing groups or any combination of these substituent groups. Examples of useful alkyl groups include methyl, ethyl, isopropyl, tertiary butyl, amyl, octyl, and nonyl. Useful cycloalkyl groups include saturated rings having 3 or more carbon atoms such as cyclopentyl, cyclohexyl and cyclododecyl. The cycloalkyl groups can also have substituent groups such as set forth herein. Useful alkenyl groups include vinyl, allyl, isopropenyl, isoprene, and butenyls, the butadienes, and the hexenes. Cycloalkenyl groups useful as phenol substituents include rings having one or more double bonds such as cyclopentenyl, cyclohexenyl and cyclododecenyl. The cycloalkenyls can also have substituent groups such as those set forth herein. Examples of useful aryl groups include benzene, naphthalene and other condensed unsaturated ring systems. Examples of substituents found on substituted aryl compounds include alkyl, alkenyl, cyclic compounds, halogens, and sulfur, oxygen or nitrogen containing substituents, or combinations of any of these. Sulfur containing groups are also useful as substituents for phenol and examples of these are sulfones, sulfoxides, sulfites and sulfates. Nitrogen containing groups useful with substituted phenols include nitrates, nitriles, amines and cyano groups. Groups containing oxygen are also useful as phenol substituents, examples of such oxygen containing groups include methoxy, ethoxy, and other carbon containing alkane and alkene chains having a hydroxyl group thereon. Aldehydes, ketones and carboxylic acids are examples of other oxygen containing substituent groups among many, which can be used with phenol. Further, the substituted phenol can be polyhydric containing more than one hydroxy group. Another useful group of phenol substituents are the halogens, examples of which include fluorine, chlorine, bromine and iodine. Presently preferred substituted phenol salts include sodium dinonyl phenate, sodium 2,4-dichlorophenate, potassium phenate and sodium O-phenylphenate.

The sodium salt of the phenol or substituted phenol is preferred, however, other alkali or alkaline earth metal salts such as potassium, calcium, lithium, magnesium, aluminum or barium, can also be used.

The rate of inhibition of the oxidation reaction and the increase of selectivity to the hydroperoxide varies with the particular phenol used. Thus some phenols must be used in smaller quantities than others since their inhibitory effect on the oxidation is higher than others. However, generally the quantity of added phenol can vary from about 0.005 to about 0.5 percent by weight of the cyclohexylbenzene and preferably from about 0.01 to about 0.1 percent by weight of the cyclohexylbenzene.

It has been found that the use of the alkali or alkaline earth metal salt of phenol or substituted phenol results in a smaller quantity of unwanted by-products being present in the reaction mixture after oxidation. The smaller quantity of unwanted by-products not only increases the selectivity to the desired hydroperoxide but also facilitates the separation of the wanted hydroperoxide from the reaction mixture and also reduces the difficulty in purifying the desired hydroperoxide.

The oxygen containing gas used preferably comprises air, however, gases containing large portions of oxygen combined with inert gases, can also be used. Preferably the oxygen content of the gas is between about 30 and 90 percent by volume. Generally the gas is bubbled through the reaction mixture, preferably accompanied by stirring to insure the contacting of the oxygen containing gas with the cyclohexylbenzene. Preferably, the reaction mixture contains no solvent or water. However, solvents which are not readily oxidized by the oxygen can be used. Such solvents are well known in the art.

The oxidation can be carried out at a temperature between about 80° and 140° C., but is preferably at a temperature between about 100° and 130° C. The oxidation can be carried out at atmospheric pressure, at a pressure of a few atmospheres under vacuum or can be carried out at a super atmospheric pressure of several atmospheres.

The 1-phenyl cyclohexylhydroperoxide can be conventionally separated from the reaction mixture and used as desired. An important use for the hydroperoxide is the formation of phenol and cyclohexanone by acid cleavage as set forth in coassigned U.S. Pat. No. 3,959,381. A preferred acid for this process includes strong acids such as the mineral acids, the alkane sulfonic acids, and the benzene and substituted benzene sulfonic acids. Other methods of acid cleavage are also well known in the art.

The following examples illustrate the method of the present invention but are not meant to limit it.

EXAMPLE I (Comparative)

A resin flask was fitted with a water cooled condenser, a mechanical stirrer, a fritted glass addition tube, and a thermometer. About 0.46 mole of cyclohexylbenzene, and about 0.1 gram of the sodium salt of cumene hydroperoxide were introduced into the flask and the mixture was heated to a temperature of about 120° C. No phenol inhibitor was added. Air was bubbled through the reaction mixture at a rate of about 52 milliliters of air per minute, while the reaction mixture was stirred. The reaction was allowed to continue for about 5 hours with the temperature maintained at about 120° C. The mixture was then cooled to room temperature, the total hydroperoxide content was determined by iodometric titration, while the percentage of the cyclohexylbenzene converted to the 1-phenyl cyclohexylhydroperoxide and the selectivity to the desired hydroperoxide were both determined by vapor phase chromatography. The results of Example I are set forth in the Table.

The Table sets forth the alkali phenol added, its weight in grams, the percentage of cyclohexylbenzene converted to 1-phenyl cyclohexylhydroperoxide, the selectivity to the desired 1-phenyl cyclohexylhydroperoxide in percent as measured by vapor phase chromatography, and the selectivity in percent to all hydroperoxides as measured by iodometric titration. By comparing the selectivity to the 1-phenyl cyclohexylhydroperoxide as measured by vapor phase chromatography, to the selectivity to all hydroperoxides as measured by iodometric titration, one can determine the percentage of unwanted hydroperoxide by-products produced by a given oxidation. The smaller the difference between the two selectivities, the less hydroperoxide by-products are present.

EXAMPLE II (Comparative)

About 0.46 mole of cyclohexylbenzene was oxidized as in Example I except that the reaction was allowed to continue for about 8.25 hours and the flow of air varied between about 50 and 60 milliliters per minute. The results were determined as in Example I and are set forth in the Table. From the Table it can be seen that increasing the reaction time in Example II from that of Example I resulted in tripling of the percentage of product converted to the desired 1-phenyl cyclohexylhydroperoxide. However, there was a decrease in the selectivity to the desired hydroperoxide and an increase in the percentage of the unwanted hydroperoxides produced.

EXAMPLE III

A resin flask was fitted with a water condenser, a mechanical stirrer, a fritted glass addition tube and a thermometer. About 0.45 mole of cyclohexylbenzene, about 0.11 gram of the sodium salt of cumene hydroperoxide and about 0.05 gram of sodium phenate were added to the resin flask. The contents were heated to a temperature of about 120° C., stirred, and air was bubbled through the mixture at a rate of about 52 milliliters per minute. The reaction was allowed to continue for about 9 hours. Results of the reaction are set forth on the Table. From the Table it can be seen that the percentage of cyclohexylbenzene converted to the desired hydroperoxide is lower than without the presence of the sodium phenate as set forth in Example II. However, the selectivity to the desired hydroproxide is much higher than in Example II and further, the percentage of unwanted hydroperoxide as shown by the iodometric determination is much smaller than in Examples I or II.

EXAMPLE IV

About 0.46 moles of cyclohexylbenzene was oxidized as in Example III; however, instead of the sodium phenate, about 0.05 gram of sodium dinonyl phenate was used and the reaction was allowed to continue for about 19.3 hours at a temperature of about 110° C. and at an air flow rate of about 45 milliliters per minute. The results are set forth on the Table. From the results of Example IV it can be seen that the sodium dinonyl phenate was such a stronger inhibitor to and that almost none of the cyclohexylbenzene was oxidized.

EXAMPLE V

About 0.48 mole of cyclohexylbenzene was oxidized, as in the other examples, with the use about of 0.1 gram of the sodium salt of cumene hydroperoxide but only with about 0.007 gram of sodium dinonyl phenate, instead of the 0.05 gram that was used in Example IV. The reaction occured at a temperature of about 110° C. for about 14.6 hours and at a flow rate of about 50 milliliters of air per minute. From the results set forth in the Table, it can be seen that the use of a much smaller quantity of the inhibitor produced a useful conversion rate with a very high selectivity to the desired hydroperoxide and the desired production of a very small quantity of unwanted hydroperoxide.

EXAMPLE VI

About 0.41 mole of cyclohexylbenzene was oxidized as in Example I with about 0.13 gram of the sodium salt of cumene hydroperoxide and about 0.05 gram of sodium 2,4-dichlorophenate. The oxidation was carried out for about 8 hours at a temperature of about 120° C. and at a flow of about 50 milliliters per minute of air. From the results set forth on the Table it can be seen that a good conversion was achieved with a high selectivity to the desired hydroperoxide and with the production of only a small quantity of unwant hydroperoxide.

EXAMPLE VII

About 0.38 mole of cyclohexylbenzene was oxidized as in Example I using about 0.08 gram of the sodium salt of cumene hydroperoxide and about 0.03 gram of sodium O-phenylphenate. The reaction was carried for about 15.5 hours at a temperature of about 100° C. and at an air flow of about 70 milliliters per minute.

From Examples I and II it can be seen that cyclohexylbenzene can be oxidized using the sodium salt of cumene hydroperoxide. However, without the additional alkali salt of phenol or a substituted phenol, there is a poor selectivity to the desired hydroperoxide with a production of relatively large quantities of undesirable hydroperoxide by-products. From Examples III through VII it can be seen that the use of a sodium salt of a phenol or a substituted phenol at a low concentration produces a conversion to the desired hydroperoxide at a lower rate than in Example II, but at a much higher selectivity to the desired hydroperixode and with a reduction in the quantity of undesirable hydroperoxides produced. This makes it easier to separate out the desired hydroperoxide from the reaction by-products with less contamination of the product and reaction materials.

TABLE

| | AIR OXIDATION OF CYCLOHEXYLBENZENE | | | |
|---|---|---|---|---|
| | | Conversion To 1-Phenyl Cyclohexyl- | Selectivity In Percent As Measured By | |
| Example | Alkali Phenol Added In Gram | Hydroperoxide In Percent | Vapor Phase Chromatography | Iodometric Titration |
| I | None 0 | 8.57 | 76.6 | 89.1 |
| II | None 0 | 24.3 | 59.9 | 70.3 |
| III | Sodium Phenate 0.05 | 14.4 | 82.8 | 87.2 |
| IV | Sodium Dinonyl 0.05 Phenate | 0.14 | — | — |
| V | Sodium Dinonyl 0.007 Phenate | 14.9 | 88.5 | 92.9 |
| VI | Sodium 2,4- 0.05 Dichlorophenate | 15.2 | 78.1 | 84.1 |
| VII | Sodium 0.03 O—Phenylphenate | 12.1 | 85.9 | 98.4 |

The above examples are for illustrative purposes only and not meant to limit the invention which is set forth in the following claims.

What is claimed is:

1. A method of preparing 1-phenyl cyclohexylhydroperoxide comprising the step of contacting a mixture comprising cyclohexylbenzene, between about 0.01 and 1 percent by weight of an alkali or alkaline earth metal salt of cumene hydroperoxide, between about 0.005 and about 0.5 percent by weight of an alkali or alkaline earth metal salt of phenol or a substituted phenol with an oxygen containing gas under reaction conditions of a temperature between about 80° and 140° C. and a pressure of at least one atmosphere effective to form said 1-phenyl cyclohexylhydroperoxide.

2. The method of claim 1 wherein said alkali or alkaline earth metal salt of phenol or a substituted phenol is selected from a group consisting of sodium phenate, sodium dinonyl phenate, sodium 2,4-dichlorophenate and sodium o-phenylphenate.

3. The method of claim 1 wherein said alkali or alkaline earth metal salt of cumene hydroperoxide is the sodium salt of cumene hydroperoxide.

4. The method of claim 1 wherein said oxygen containing gas comprises air.

5. The method of claim 1 wherein said reaction is carried on at a temperature between about 100° and 130° C.

6. A method of producing phenol which comprises the step of contacting said 1-phenyl cyclohexylhydroperoxide formed by the method of claim 1 with an acid cleavage catalyst.

7. A method of preparing 1-phenyl cyclohexylhydroperoxide comprising the step of contacting a mixture of cyclohexylbenzene, between about 0.01 and 1 percent by weight of a sodium salt of cumene hydroperoxide, and between 0.005 to about 0.5 percent by weight of a sodium salt of phenol or a substituted phenol with an oxygen containing gas at a temperature between about 80° C. and 140° C. and a pressure of at least one atmosphere.

8. The method of claim 7 and further comprising the step of separating said 1-phenyl cyclohexylhydroperoxide from said reaction mixture.

9. The method of claim 7 wherein said sodium salt of a phenol or a substituted phenol is selected from a group consisting of sodium phenate, sodium dinoyl phenate, sodium 2,4-dichlorophenate and sodium O-phenylphenate.

* * * * *